(12) United States Patent
Yokoyama et al.

(10) Patent No.: US 8,735,626 B2
(45) Date of Patent: May 27, 2014

(54) METHOD OF PRODUCING AROMATIC AMINO COMPOUNDS

(75) Inventors: Norimasa Yokoyama, Ibaraki (JP); Makoto Nagaoka, Ibaraki (JP); Kazunori Togashi, Ibaraki (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 152 days.

(21) Appl. No.: 13/123,098

(22) PCT Filed: Jan. 25, 2010

(86) PCT No.: PCT/JP2010/050922
§ 371 (c)(1),
(2), (4) Date: Apr. 7, 2011

(87) PCT Pub. No.: WO2010/090094
PCT Pub. Date: Aug. 12, 2010

(65) Prior Publication Data
US 2011/0257404 A1    Oct. 20, 2011

(30) Foreign Application Priority Data
Feb. 9, 2009    (JP) .................................. 2009-027132

(51) Int. Cl.
C07C 211/00    (2006.01)
C07C 59/00    (2006.01)
C07C 65/21    (2006.01)

(52) U.S. Cl.
USPC ......................................... 564/305; 562/470

(58) Field of Classification Search
None
See application file for complete search history.

(56) References Cited

U.S. PATENT DOCUMENTS

| | | | |
|---|---|---|---|
| 5,929,281 A | 7/1999 | Nishiyama et al. | |
| 6,242,648 B1 | 6/2001 | Yamasaki et al. | |
| 6,759,554 B2 * | 7/2004 | Buchwald et al. | 564/192 |
| 6,762,329 B2 * | 7/2004 | Marcoux et al. | 568/635 |
| 7,273,953 B2 | 9/2007 | Kubo et al. | |
| 2006/0069287 A1 | 3/2006 | Kubo et al. | |

FOREIGN PATENT DOCUMENTS

| | | |
|---|---|---|
| CA | 2445159 | 10/2002 |
| JP | 11-087061 | 3/1999 |
| JP | 2000-256276 | 9/2000 |
| JP | 3161360 | 2/2001 |
| JP | 2004-536798 | 12/2004 |
| JP | 2005-239671 | 9/2005 |
| JP | 2005-350416 | 12/2005 |
| JP | 2006-16321 | 1/2006 |
| WO | 2004/024670 | 3/2004 |

OTHER PUBLICATIONS

Antilla et al., "Copper-Diamine-Catalyzed..", J. Org. Chem., 2004, pp. 5578-5587.
Jiang et al., "CuBr/rac . . . ", J. Org. Chem., 2007, pp. 72, 672-674.
Ullmann, "Ueber eine neue . . . ", Chemische Berichte, 1903, pp. 2382-2384.
Ley et al., "Modern Synthetic . . .", Angew. Chem. Inst. Ed., 2003, pp. 5400-5449.
Antilla et al., "The Copper-Catalyzed . . . ", J.Am. Chem. Soc., 2002, pp. 11684-11688.
Extended European Search Report (EESR) in European Patent Application No. 10741075.5, dated Feb. 11, 2013.

* cited by examiner

*Primary Examiner* — Clinton Brooks
(74) *Attorney, Agent, or Firm* — Greenblum & Bernstein, P.L.C.

(57) ABSTRACT

A method of producing an aromatic amino compound using a primary or secondary amine compound and a halogenated aromatic compound as starting materials, and relying upon the Ullmann reaction, the method being capable of obtaining the highly pure aromatic amino compound in high yields and inexpensively. A primary or secondary amine compound having an aromatic ring group and a halogenated aromatic compound as starting materials, are reacted with the halogenated aromatic compound in the presence of copper catalyst and base to produce the aromatic amino compound having a structure in which an aromatic ring group derived from the halogenated aromatic compound is coupled to the amino group of the amine compound, wherein the amine compound and the halogenated aromatic compound are reacted together such that an aromatic oxycarboxylic acid having a hydroxyl group and a hydroxycarbonyl group bonded to neighboring carbon atoms, is present together with the copper catalyst and the base.

7 Claims, 1 Drawing Sheet

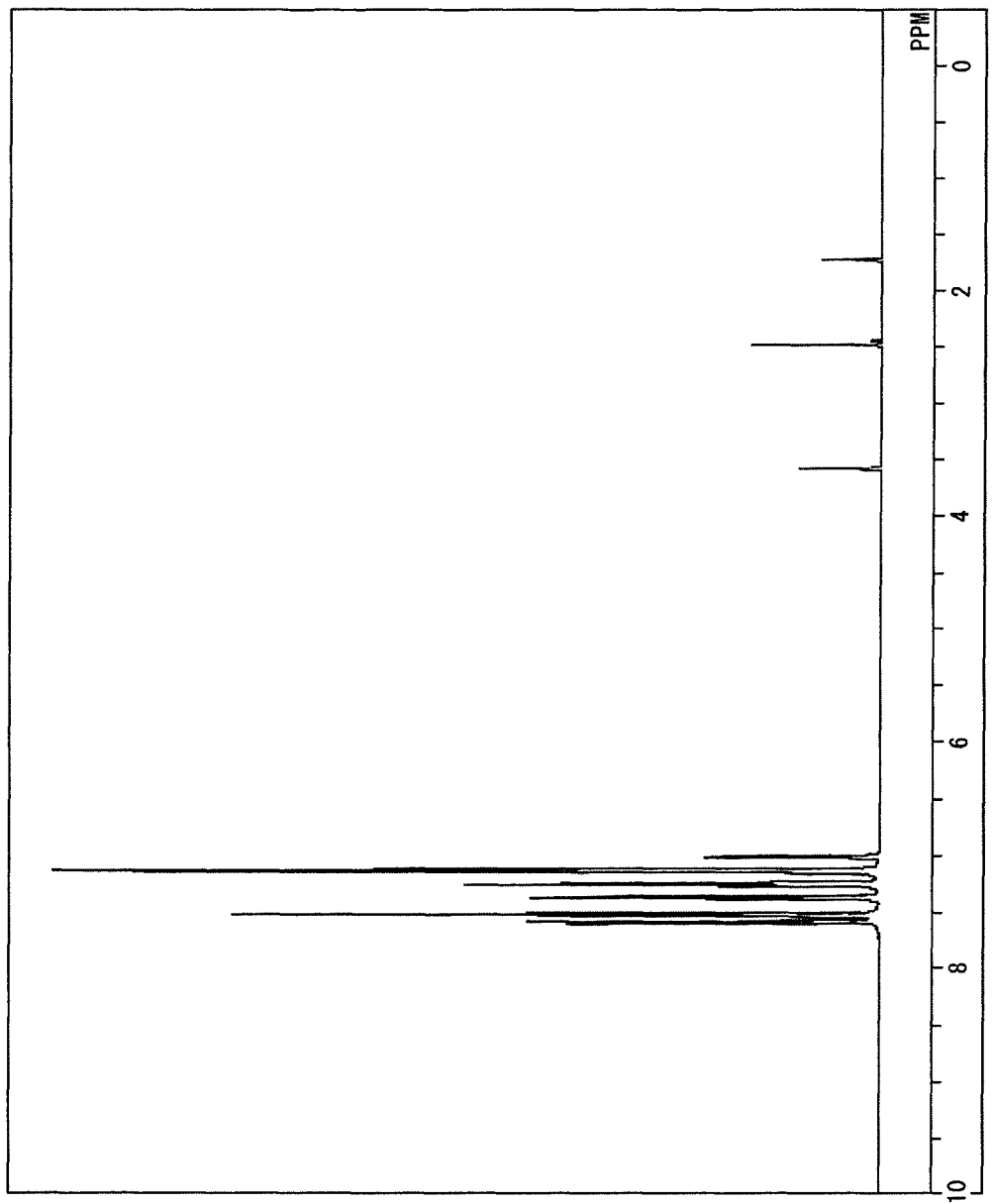

METHOD OF PRODUCING AROMATIC AMINO COMPOUNDS

TECHNICAL FIELD

This invention relates to a method of producing aromatic amino compounds which are useful as various organic materials or intermediate products for producing organic materials.

BACKGROUND ART

Aromatic amino compounds as represented by an arylamine and, particularly, a triarylamine and a diarylamine are useful as starting materials of medical and agricultural chemicals, as organic functional materials and as intermediate products therefor. In recent years, they have been used as organic EL materials and organic electrically conducting materials or intermediate products therefor, and are finding ever increasing importance.

As a method of synthesizing the triarylamine and the diarylamine, there has been known, for example, a method that reacts an aryl halide with a monoarylamine by using a copper catalyst. The above reaction has been called Ullmann reaction (see, for example, a non-patent document 1).

However, the Ullmann reaction requires a high reaction temperature and is accompanied by such defects that the obtained aromatic amino compounds (e.g., triarylamine and diarylamine) are colored conspicuously and that the yields are, usually, low due to the formation of by-products in large amounts. Besides, the obtained aromatic amino compounds must be refined requiring much work causing a defect of an increased cost of production.

In order to improve such defects, attempts have been made to lower the reaction temperature by adding a compound that can be coordinated in copper which is a reaction catalyst so that the object product can be obtained maintaining a high purity. For example, there have been reported methods capable of obtaining in high yields the object aromatic amino compounds through the reaction at such relatively low temperatures as 110 to 135° C. by adding a phenanthroline, a bipyridyl or a diamine compound such as cyclohexanediamine (see, for example, non-patent documents 2 to 4).

There has, further, been reported an example of conducting a reaction by adding a 1,1'-binaphthyl-2,2'-diol (see, for example, a non-patent document 5).

According to these examples, the reaction can be conducted under mild conditions and, besides, the object product can be obtained in good yields. However, the compound to be added is so expensive that there remains a problem from the standpoint of cost of production hindering the way toward putting the methods into practice.

There has, further, been known a method of conducting the reaction by increasing the basicity of the reaction system by adding a crown ether (see, for example, a patent document 1). However, the crown ether, too, is an expensive compound which makes the production method never advantageous from the standpoint of cost, and does not make the production method practicable.

There has, further, been known the Ullmann reaction for forming an alkylarylamine by reacting an alkylamine with an aryl halide in the presence of a copper catalyst, and there has been reported an example of the Ullmann reaction using an aromatic oxycarboxylic acid (concretely, a 2-hydroxybenzenecarboxylic acid) having a hydroxyl group and a hydroxycarbonyl group bonded to the neighboring carbon atoms thereof (see non-patent document 5). According to this example, however, the object product was not at all obtained, and no effect was recognized despite of using the aromatic oxycarboxylic acid.

There has, further, been proposed a method of producing an arylamine relying on the Buchwald-Hartwig reaction by using, as a catalyst, palladium-phosphine complex that has a trialkylphosphine as a ligand (see, for example, a patent document 2). According to this production method, however, the reaction must be conducted in a strictly controlled inert gas atmosphere to maintain activity of the palladium-phosphine complex. Besides, the trialkylphosphine itself which serves as a ligand is very unstable in the air, and must be stored and weighed in the inert gas atmosphere hindering the attempt for putting the method into practice. Besides, palladium is very expensive and the phosphine compound used as the ligand is expensive, too, making it difficult to place the method in practice.

PRIOR ART DOCUMENTS

Patent Documents

Patent document 1: JP-A-11-87061
Patent document 2: Japanese Patent No. 3161360

Non-patent Documents

Non-patent document 1: Chemische Berichte, 36, 2382 (1903)
Non-patent document 2: Angew. Chem. Int. Ed., 42, 5400 (2003)
Non-patent document 3: J. Am. Chem. Soc., 124, 11684 (2002)
Non-patent document 4: J. Org. Chem., 69, 5578 (2004)
Non-patent document 5: J. Org. Chem., 72, 672 (2007)

OUTLINE OF THE INVENTION

Problems that the Invention is to Solve

It is, therefore, an object of the present invention to provide a method of producing an aromatic amino compound by the Ullmann reaction by using a primary or secondary amine compound and a halogenated aromatic compound as starting materials, the method being capable of producing the highly pure aromatic amino compound in high yields and inexpensively.

Means for Solving the Problems

Namely, according to the present invention, there is provided a method of producing an aromatic amino compound by using, as starting materials, an amine compound represented by the following general formula (1):

wherein
R is a hydrogen atom or an aromatic ring group, and
Ar is an aromatic ring group,
and a halogenated aromatic compound; and reacting the amine compound with the halogenated aromatic compound in the presence of a copper catalyst and a base so as to produce the aromatic amino compound having a structure in which an aromatic ring group derived from the halogenated aromatic compound is coupled to the amino group of the amine compound;

wherein the amine compound and the halogenated aromatic compound are reacted together under a condition where an aromatic oxycarboxylic acid having a hydroxyl group and a hydroxycarbonyl group that are bonded to the neighboring carbon atoms thereof, is made present together with the copper catalyst and the base.

In the production method of the present invention, it is desired that:

(1) The halogen atom of the halogenated aromatic compound is iodine, bromine or chlorine;
(2) The halogenated aromatic compound is an aryl iodide, an aryl bromide or an aryl chloride; and
(3) The starting amine compound is monoarylamine or diarylamine.

Further, the aromatic oxycarboxylic acid used in the present invention is, preferably, (4) a compound represented by the following general formula (2),

[Chemical 1]

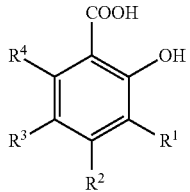

(2)

Wherein
$R^1$ to $R^4$ are hydrogen atoms; alkyl groups having 1 to 6 carbon atoms; cycloalkyl groups having 5 to 8 carbon atoms; alkenyl groups having 2 to 6 carbon atoms; alkynyl groups having 2 to 6 carbon atoms; alkyloxy groups having 1 to 6 carbon atoms; cycloalkyloxy groups having 5 to 8 carbon atoms; di-substituted amino groups having, as a substituent, an alkyl group with 1 to 6 carbon atoms or an aromatic hydrocarbon group; hydroxyl groups; formyl groups; alkoxycarbonyl groups; hydroxycarbonyl groups; cyano groups; nitro groups; trifluoromethyl groups; fluorine atoms; aryloxy groups; aromatic hydrocarbon groups; or aromatic heterocyclic ring groups; and $R^1$ and $R^2$, $R^2$ and $R^3$, or $R^3$ and $R^4$ may be bonded together to form a ring;

(5) a compound represented in the general formula (2), wherein at least one of the groups $R^1$ to $R^4$ is a straight-chain or branched-chain alkyl group having 1 to 6 carbon atoms, a cycloalkyl group having 5 to 8 carbon atoms, an aromatic hydrocarbon group or an aromatic heterocyclic ring group; or (6) a 3,5-di-tert-butyl-2-hydroxybenzenecarboxylic acid.

Effects of the Invention

According to the present invention, the Ullmann reaction is proceeded in the presence of the aromatic oxycarboxylic acid together with the copper catalyst and the base making it possible to lower the reaction temperature, to terminate the reaction in a shortened period of time, and to obtain a desired aromatic amino compound in high yields and in a highly pure form.

Achievement of the above effects by using the aromatic oxycarboxylic acid was found as a phenomenon as a result of conducting extensive experiments. Though the reason has not been clarified yet, the inventors consider that the effects are stemming from the interaction between the aromatic oxycarboxylic acid with copper used as the reaction catalyst and, therefore, from the improved catalytic activity of copper.

Further, the above aromatic oxycarboxylic acid, e.g., 2-hydroxybenzenecarboxylic acid and the like are cheaply available, and can be used for the reaction requiring no special operation or apparatus, offering advantage from the standpoint of production cost. Therefore, the production method of the present invention can be very advantageously put into practice on an industrial scale.

BRIEF DESCRIPTION OF THE DRAWINGS

FIG. 1 is a 1H-NMR chart of a compound synthesized in Example 1.

MODE FOR CARRYING OUT THE INVENTION

According to the present invention, the aromatic amino compound is produced by the Ullmann reaction by using the amine compound represented by the above general formula (1) and the halogenated aromatic compound as starting materials. Here, the reaction can be expressed, for example, by the following formulas,

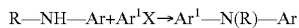

or

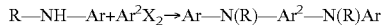

wherein
R and Ar are as defined in the above formula (1),
X is a halogen atom derived from the halogenated aromatic compound;
$Ar^1$ is a monovalent aromatic ring group derived from the halogenated aromatic compound; and
$Ar^2$ is a divalent aromatic ring group derived from the halogenated aromatic compound.

The above reaction formula is a case of when a halogenated aromatic compound having one or two halogen atoms is used as a starting material. It will be also easily learned that when a halogenated aromatic compound having three or more halogen atoms is used, too, the amino group reacts with the halogen atoms in the same manner as described above, and a corresponding aromatic amino compound is obtained.

When the group R possessed by the starting amine compound is a hydrogen atom, e.g., in the case of a monoarylamine, there will be obtained a diarylamine according to the above reaction formula. Here, the diarylamine has a group NH. Upon further executing the Ullmann reaction, therefore, there will be synthesized a triarylamine.

In the Ullmann reaction of the amine compound with the halogenated aromatic compound, it is important to use the aromatic oxycarboxylic acid having a hydroxyl group and a hydroxycarbonyl group bonded to the neighboring carbon atoms thereof in the presence of the copper catalyst and the base. Compounds used for the reaction and the reaction conditions will be described below in detail.

<Starting Compounds>
1. Amine Compounds

The amine compound used as a starting material in the present invention is represented by the following general formula (1):

 (1)

wherein
R is a hydrogen atom or an aromatic ring group, and
Ar is an aromatic ring group.

That is, as the hydrogen atom bonded to the nitrogen atom in the above general formula (1) is split off upon being reacted with a halogen atom of the halogenated aromatic compound, the aromatic ring group in the halogenated aromatic compound is coupled.

In the above general formula (1), the aromatic ring groups denoted by R and Ar may be aromatic hydrocarbon groups or aromatic heterocyclic ring groups.

As the aromatic hydrocarbon group (aryl group), there can be exemplified phenyl group, biphenylyl group, terphenylyl group, tetrakisphenyl group, styryl group, naphthyl group, anthryl group, acenaphthenyl group, fluorenyl group, phenanthryl group, indenyl group and pyrenyl group.

As the aromatic heterocyclic ring group, there can be exemplified pyridyl group, triazil group, pyrimidyl group, furanyl group, pyronyl group, thiophenyl group, quinolyl group, isoquinolyl group, benzofuranyl group, benzothiophenyl group, indolyl group, carbozolyl group, benzoxazolyl group, benzothiazolyl group, quinoxalyl group, benzoimidazolyl group, pyrazolyl group, dibenzofuranyl group, dibenzothiophenyl group, naphthyridinyl group, phenanthrolinyl group and acridinyl group.

The above aromatic hydrocarbon groups and aromatic heterocyclic ring groups may, further, have various substituents other than the halogen atoms so far as they do not impair the Ullmann reaction. As such substituents, there can be exemplified cyano group, hydroxyl group, nitro group, straight-chain or branched-chain alkyl group having 1 to 6 carbon atoms mentioned above, straight-chain or branched-chain alkyloxy group having 1 to 6 carbon atoms mentioned above, amino group, trifluoromethyl group, phenyl group, biphenylyl group, terphenylyl group, naphthyl group, phenanthryl group, aralkyl group, fluorenyl group, indenyl group, pyridyl group, pyrimidyl group, furanyl group, pyronyl group, thiophenyl group, quinolyl group, benzofuranyl group, benzothiophenyl group, indolyl group, carbazolyl group, benzoxazolyl group, quinoxalyl group, benzimidazolyl group, pyrazolyl group, dibenzofuranyl group and dibenzothiophenyl group. These substituents may, further, have substituents.

The starting amine compound preferably used in the present invention is a monoarylamine (R=hydrogen atom, Ar=aromatic hydrocarbon group) or a diarylamine (R=aromatic hydrocarbon group, Ar=aromatic hydrocarbon group). Of them, the diarylamine is most preferred.

2. Halogenated Aromatic Compounds

The halogenated aromatic compound to be reacted with the above amine compound is a compound in which one or two or more halogen atoms are bonded as substituents to the aromatic ring group thereof. Example of the aromatic ring group include an aromatic hydrocarbon group and an aromatic heterocyclic ring group like those represented by the above general formula (1).

Example of the aromatic hydrocarbon group include phenyl group, biphenylyl group, terphenylyl group, tetrakisphenyl group, styryl group, naphthyl group, anthryl group, acenaphthenyl group, fluorenyl group, phenanthryl group, indenyl group, pyrenyl group, and polyvalent groups such as divalent, trivalent and tetravalent groups corresponding to the above groups depending on the number of halogen atoms bonded thereto.

Examples of the aromatic heterocyclic ring groups include pyridyl group, triazil group, pyrimidyl group, furanyl group, pyronyl group, thiophenyl group, quinolyl group, isoquinolyl group, benzofuranyl group, benzothiophenyl group, indolyl group, carbazolyl group, benzoxazolyl group, benzothiazolyl group, quinoxalyl group, benzoimidazolyl group, pyrazolyl group, dibenzofuranyl group, dibenzothiophenyl group, naphthyridinyl group, phenanthrolinyl group, acridinyl group and polyvalent groups such as divalent, trivalent and tetravalent groups corresponding to the above groups depending on the number of halogen atoms bonded thereto.

The above aromatic hydrocarbon groups and aromatic heterocyclic ring groups, too, may, further, have various substituents other than the halogen atoms so far as they do not impair the Ullmann reaction. As such substituents, there can be exemplified cyano group, hydroxyl group, nitro group, straight-chain or branched-chain alkyl group having 1 to 6 carbon atoms mentioned above, straight-chain or branched-chain alkyloxy group having 1 to 6 carbon atoms mentioned above, amino group, trifluoromethyl group, phenyl group, biphenylyl group, terphenylyl group, naphthyl group, phenanthryl group, aralkyl group, fluorenyl group, indenyl group, pyridyl group, pyrimidyl group, furanyl group, pyronyl group, thiophenyl group, quinolyl group, benzofuranyl group, benzothiophenyl group, indolyl group, carbazolyl group, carbolyl group, benzoxazolyl group, quinoxalyl group, benzimidazolyl group, pyrazolyl group, dibenzofuranyl group and dibenzothiophenyl group. These substituents may, further, have another substituents.

The halogen atom bonded to the above aromatic ring group is iodine, bromine or chlorine, but fluorine is excluded from the standpoint of reactivity. Further, a plurality of different halogen atoms may be bonded to the aromatic ring group. The halogen atom most desired for the present invention is iodine or bromine from the standpoint of reactivity.

In the present invention, the ratio of amounts of the amine compound and the halogenated aromatic compound used as starting materials may be determined depending upon the kind of the object aromatic amino compound, number of halogen atoms possessed by the halogenated aromatic compound and the number of NH groups possessed by the amine compound while taking the cost of production, reaction yields and the like into consideration. When a diarylamine is to be produced by using a monoarylamine as the amine compound, for example, the amine compound and the halogenated aromatic compound are used in such amounts that the NH groups are 1 to 20 equivalents and, preferably, 1 to 10 equivalents per equivalent of halogen atoms. Further, when a triarylamine is to be produced, the amine compound and the halogenated aromatic compound may be used in such amounts that the NH groups are 0.05 to 0.5 equivalents and, preferably, 0.25 to 0.5 equivalents per equivalent of halogen atoms.

<Copper Catalysts>

In the present invention, there is no particular limitation on the copper catalyst, and there can be used any known one that has been used in the Ullmann reaction. Concrete examples thereof include copper powder, cuprous chloride, cupric chloride, cuprous bromide, cupric bromide, copper iodide, cuprous oxide, cupric oxide, copper sulfate, copper nitrate, copper carbonate, copper acetate and copper hydroxide. Particularly preferred examples are copper powder, cuprous chloride, cuprous bromide and copper iodide.

In the present invention, when the amino group in the amine compound used as the starting material is $NH_2$ (R=H), the copper catalyst is used in an amount in a range of 0.02 to 2 mols and, particularly, 0.1 to 1 mol per mol of the amine compound. Further, when the amino group in the amine compound used as the starting material is NH(R=aromatic ring group), the copper catalyst is used desirably in an amount in a range of 0.01 to 1 mol and, particularly, 0.05 to 0.5 mols per mol of the amine compound.

<Bases>

The base is used for dehalogenation. Though there is no particular limitation, there can be used, for example, alkali metal carbonates, alkali metal phosphates, alkali metal hydroxides, alkaline earth metal hydroxides and metal alkoxides.

As the alkali metal carbonates, there can be exemplified sodium carbonate, lithium carbonate, cesium carbonate and potassium carbonate.

As the alkali metal phosphates, there can be exemplified sodium phosphate, potassium phosphate, cesium phosphate and lithium phosphate.

As the alkali metal hydroxides, there can be exemplified sodium hydroxide, lithium hydroxide, potassium hydroxide and cesium hydroxide.

As the alkaline earth metal hydroxides, there can be exemplified barium hydroxide, etc.

As the metal alkoxides, there can be exemplified sodium methoxide, sodium ethoxide, sodium-tert-butoxide and potassium-tert-butoxide.

In the present invention, there are particularly preferably used sodium hydroxide, potassium hydroxide, potassium phosphate and potassium carbonate.

When the amino group in the amine compound is $NH_2$ (R=H), the base is used for the reaction desirably in an amount in a range of 2 to 10 mols and, particularly, 2.2 to 6 mols per mol of the amine compound. Further, when the amino group in the amine compound used as the starting material is NH(R=aromatic ring group), the base is used desirably in an amount in a range of 1 to 5 mols and, particularly, 1.1 to 3 mols per mol of the amine compound.

If the amount of the base is less than the above range, the aromatic amino compound is obtained in a decreased yield. Further, even if the base is used in excess amounts for the reaction, there is no effect on the yield of the aromatic amino compound that is obtained but a complicated after-treatment operation is required after the reaction has been finished, which is not desirable.

<Aromatic Oxycarboxylic Acids>

In the present invention, the amine compound and the halogenated aromatic compound are reacted together under a condition where an aromatic oxycarboxylic acid having a hydroxyl group and a hydroxycarbonyl group that are bonded to the neighboring carbon atoms thereof is made present, for example, the aromatic oxycarboxylic acid represented by the following general formula (2), is made present together with the above copper catalyst and the base.

[Chemical 2]

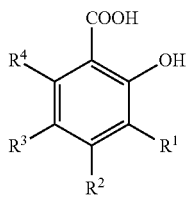

(2)

In the above general formula (2), $R^1$ to $R^4$ are hydrogen atoms; alkyl groups; cycloalkyl groups; alkenyl groups; alkynyl groups; alkyloxy groups; cycloalkyloxy groups; di-substituted amino groups having, as a substituent, an alkyl group or an aromatic hydrocarbon group; hydroxyl groups; formyl groups; alkoxycarbonyl groups; hydroxycarbonyl groups; cyano groups; nitro groups; trifluoromethyl groups; fluorine atoms; aryloxy groups; aromatic hydrocarbon groups; or aromatic heterocyclic ring groups; and $R^1$ and $R^2$, $R^2$ and $R^3$, or $R^3$ and $R^4$ may be bonded together to form a ring.

Of the above $R^1$ to $R^4$, the alkyl groups may assume the form of either a straight chain or a branched chain, and have 1 to 6 carbon atoms. The same also holds for the alkyl group possessed, as a substituent, by the di-substituted amino groups.

As the alkyl group, there can be exemplified methyl group, ethyl group, n-propyl group, isopropyl group, n-butyl group, 2-methylpropyl group, tert-butyl group, n-pentyl group, 3-methylbutyl group, neopentyl group, tert-pentyl group, 2-methylbutyl group, n-hexyl group, 4-methylpentyl group, 3-methylpentyl group and ethylbutyl group.

The above cycloalkyl group has 5 to 8 carbon atoms, and concrete examples thereof include cyclopentyl group, cyclohexyl group, cycloheptyl group, cyclooctyl group, 3-methylcyclohexyl group, 4-methylcyclohexyl group and 4-ethylcyclohexyl group.

The above alkenyl group may assume the form of either a straight chain or a branched chain, and has 2 to 6 carbon atoms. Concrete examples thereof include vinyl group, allyl group, isopropenyl group, 2-butenyl group, 2-methylallyl group, 1,1-dimethylallyl group, 3-methyl-2-butenyl group, 3-methyl-3-butenyl group, 4-pentenyl group and hexenyl group.

The above alkynyl group may assume the form of either a straight chain or a branched chain, and has 2 to 6 carbon atoms. Concrete examples thereof include ethynyl group, 1-propynyl group, 2-propynyl group, 1-butynyl group, 1-pentynyl group, 1-hexynyl group, 5-hexynyl group, 3-methyl-1-butynyl group and 1,1-dimethyl-2-butynyl group.

The above alkyloxy group may assume the form of either a straight chain or a branched chain, and has 1 to 6 carbon atoms. Concrete examples thereof include methoxy group, ethoxy group, n-propoxy group, isopropoxy group, n-butoxy group, isobutoxy group, tert-butoxy group, n-pentyloxy group, isopentyloxy group, neopentyloxy group, tert-pentyloxy group, 2-methylbutyloxy group, n-hexyloxy group, 4-methylpentyloxy group, 3-methylpentyloxy group and ethylbutyloxy group.

The above cycloalkyloxy group has 5 to 8 carbon atoms, and concrete examples thereof include cyclopentyloxy group, cyclohexyloxy group, cycloheptyloxy group, cyclooctyloxy group, 3-methylcyclohexyloxy group, 4-methylcyclohexyloxy group and 4-ethylcyclohexyloxy group.

As the above alkoxycarbonyl group, there can be exemplified methoxycarbonyl group, ethoxycarbonyl group, n-propoxycarbonyl group, isopropoxycarbonyl group, n-butoxycarbonyl group, isobutoxycarbonyl group, tert-butoxycarbonyl group, n-pentyloxycarbonyl group, isopentyloxycarbonyl group, neopentyloxycarbonyl group, tert-pentyloxycarbonyl group, 2-methylbutyloxycarbonyl group, n-hexyloxycarbonyl group, 4-methylpentyloxycarbonyl group, 3-methylpentyloxycarbonyl group and ethylbutyloxycarbonyl group.

As the above aryloxy group, there can be exemplified phenoxy group, biphenylyloxy group, terphenylyloxy group, tetrakisphenylyloxy group, styryloxy group, naphthyloxy group, anthryloxy group, acenaphthenyloxy group, fluorenyloxy group, phenanthryloxy group, indenyloxy group and pyrenyloxy group.

As the above aromatic hydrocarbon group, there can be exemplified phenyl group, biphenylyl group, terphenylyl group, tetrakisphenyl group, styryl group, naphthyl group, anthryl group, acenaphthenyl group, fluorenyl group, phenanthryl group, indenyl group and pyrenyl group. The same also holds for the aromatic hydrocarbon group possessed as a substituent by the di-substituted amino group.

As the above aromatic heterocyclic ring group, there can be exemplified pyridyl group, pyrimidyl group, furanyl group, pyronyl group, thiophenyl group, quinolyl group, benzofuranyl group, benzothiophenyl group, indolyl group, carbazolyl group, benzoxazolyl group, quinoxalyl group, benzimidazolyl group, pyrazolyl group, dibenzofuranyl group and dibenzothiophenyl group.

In the above general formula (2), the aryloxy group, aromatic hydrocarbon group and aromatic heterocyclic ring group may have a substituent so far as they do not impair the Ullmann reaction. As the substituent, there can be exemplified cyano group, hydroxyl group, nitro group, and the above-mentioned alkyl group and alkyloxy group. There can be, further, exemplified, as the substituent, amino group, trifluoromethyl group, phenyl group, biphenylyl group, terphenylyl group, naphthyl group, phenanthryl group, aralkyl group, fluorenyl group, indenyl group, pyridyl group, pyrimidyl group, furanyl group, pyronyl group, thiophenyl group, quinolyl group, benzofuranyl group, benzothiophenyl group, indolyl group, carbazolyl group, carbolyl group, benzoxazolyl group, quinoxalyl group, benzimidazolyl group, pyrazolyl group, dibenzofuranyl group and dibenzothiophenyl group.

In the aromatic oxycarboxylic acid represented by the above general formula (2), at least one of $R^1$ to $R^4$ is desirably a straight-chain or branched-chain alkyl group having 1 to 6 carbon atoms, a cycloalkyl group having 5 to 6 carbon atoms, an aromatic hydrocarbon group or an aromatic heterocyclic ring group.

As the aromatic oxycarboxylic acid preferably used in the present invention, there can be concretely exemplified the following compounds:
2-hydroxybenzenecarboxylic acid,
3-methyl-2-hydroxybenzenecarboxylic acid,
4-methyl-2-hydroxybenzenecarboxylic acid,
5-methyl-2-hydroxybenzenecarboxylic acid,
6-methyl-2-hydroxybenzenecarboxylic acid,
3,5-dimethyl-2-hydroxybenzenecarboxylic acid,
5-ethyl-2-hydroxybenzenecarboxylic acid,
5-propyl-2-hydroxybenzenecarboxylic acid,
5-butyl-2-hydroxybenzenecarboxylic acid,
3-tert-butyl-2-hydroxybenzenecarboxylic acid,
5-tert-butyl-2-hydroxybenzenecarboxylic acid,
3,5-di(tert-butyl)-2-hydroxybenzenecarboxylic acid,
3-hexyl-2-hydroxybenzenecarboxylic acid,
5-hexyl-2-hydroxybenzenecarboxylic acid,
3-cyclohexyl-2-hydroxybenzenecarboxylic acid,
5-cyclohexyl-2-hydroxybenzenecarboxylic acid,
3,5-di-cyclohexyl-2-hydroxybenzenecarboxylic acid,
5-ethenyl-2-hydroxybenzenecarboxylic acid,
5-ethynyl-2-hydroxybenzenecarboxylic acid,
5-methoxy-2-hydroxybenzenecarboxylic acid,
5-phenoxy-2-hydroxybenzenecarboxylic acid,
4-nitro-2-hydroxybenzenecarboxylic acid,
4-fluoro-2-hydroxybenzenecarboxylic acid,
5-trifluoromethyl-2-hydroxybenzenecarboxylic acid,
5-cyano-2-hydroxybenzenecarboxylic acid,
2,3-di-hydroxybenzenecarboxylic acid,
2,4-di-hydroxybenzenecarboxylic acid,
2,5-di-hydroxybenzenecarboxylic acid,
2,6-di-hydroxybenzenecarboxylic acid,
4-phenyl-2-hydroxybenzenecarboxylic acid,
5-phenyl-2-hydroxybenzenecarboxylic acid,
5-biphenylyl-2-hydroxybenzenecarboxylic acid,
5-(pyridine-2-il)-2-hydroxybenzenecarboxylic acid,
5-naphthyl-2-hydroxybenzenecarboxylic acid,
2-hydroxynaphthalene-1-carboxylic acid,
3-hydroxynaphthalene-2-carboxylic acid,
1-hydroxynaphthalene-2-carboxylic acid,
1-hydroxyphenanthrene-2-carboxylic acid,
1-hydroxypyrene-2-carboxylic acid.

The aromatic oxycarboxylic acid most desirably used in the present invention is a compound in which $R^1$ and $R^3$ in the general formula (2) are tert-butyl groups, i.e., a 3,5-di-tert-butyl-2-hydroxybenzenecarboxylic acid.

The above aromatic oxycarboxylic acid is, usually, used in an amount of 0.1 to 10 mols, particularly, 0.5 to 5 mols and, most desirably, 0.8 to 3 mols per mol of the copper catalyst.

<Other Additives>

In the invention, there can be added, as required, a sulfite compound or a thiosulfate compound to prevent the formation of oxides as by-products.

As the sulfite compound, there can be exemplified sodium sulfite, sodium hydrogensulfite, potassium sulfite, potassium hydrogensulfite, magnesium sulfite, cesium sulfite, barium sulfite and ammonium hydrogensulfite.

As the thiosulfate compound, there can be exemplified sodium thiosulfate, sodium dithionite, sodium pyrosulfite, ammonium pyrosulfite and potassium pyrosulfite.

In the present invention, there is no particular limitation on the amount of the sulfite compound or the thiosulfate compound. When the amino group in the amine compound used as the starting material is $NH_2$ (R=H), however, it is desired that the sulfite compound or the thiosulfate compound is used in an amount in a range of 0.002 to 20 mols and, particularly, 0.02 to 10 mols per mol of the amine compound. Further, when the amino group in the amine compound used as the starting material is NH(R=aromatic ring group), it is desired that the sulfite compound or the thiosulfate compound is used in an amount in a range of 0.001 to 10 mols and, particularly, 0.01 to 5 mols per mol of the amine compound.

<Reaction (Ullmann Reaction)>

The reaction of the amine compound with the halogenated aromatic compound is, usually, carried out in a solvent in the presence of the copper catalyst, base and aromatic oxycarboxylic acid. The reaction, however, can also be carried out without using solvent.

There is no particular limitation on the solvent so far as it does not impair the reaction, and there can be used, for example, aliphatic hydrocarbon type solvent, aromatic hydrocarbon type solvent, ether type solvent, amide type solvent or sulfoxide type solvent. They can be used alone or being mixed together in two or more kinds. Preferably, there is used a solvent capable of dissolving the amine compound and the halogenated aromatic compound which are the starting materials as well as the aromatic oxycarboxylic acid of the invention having a hydroxyl group and a hydroxycarbonyl group bonded to the neighboring carbon atoms thereof.

As the aliphatic hydrocarbon type solvent, there can be exemplified octane, nonane, decane, undecane, dodecane, tridecane and tetradecane.

As the aromatic hydrocarbon type solvent, there can be exemplified toluene, xylene, mesitylene, ethylbenzene, diethylbenzene, diisopropylbenzene, hexylbenzene, octylbenzene, dodecylbenzene, methylnaphthalene, dimethylnaphthalene, 1,2,3,4-tetrahydronahthalene and nitrobenzene.

As the ether type solvent, there can be exemplified 1,4-dioxane, anisole and diphenyl ether.

As the amide type solvent, there can be exemplified dimethylformamide, dimethylacetamide, N-methylpyrrolidone and 1,3-dimethyl-2-imidazolidinone.

As the sulfoxide type solvent, there can be exemplified dimethylsulfoxide and tetrahydrothiophene-1,1-dioxide.

In the present invention, the amount of the solvent may differ depending upon the kinds of the starting materials used in the reaction but is, usually, in a range of not more than 10 parts by mass, preferably, 0.01 to 10 parts by mass and, more preferably, 0.05 to 5 parts by mass per part by mass of the starting amine compound. If the solvent is used in an amount larger than the required amount, the reaction time tends to increase and by-products tend to be formed in increased amounts. If the solvent is used in small amounts, it often happens that the reaction system becomes uneven, unreacted products are formed in increased amounts, and the yield decreases.

In the present invention, the reaction temperature is in a range of 50° C. to 300° C., preferably, 80° C. to 250° C. and, more preferably, 100° C. to 220° C. If the reaction temperature is low, the reaction time tends to increase and by-products tend to be formed in increased amounts. If the reaction temperature is high, side reaction takes place and by-products tend to be formed in increased amounts.

The reaction time varies depending upon the reaction temperature but is, usually, in a range of 0.2 to 72 hours and, particularly, 1 to 30 hours.

In the present invention, the reaction can be carried out under any conditions such as normal pressure or elevated pressure but is, usually, carried out in an inert gas atmosphere such as of nitrogen or argon with stirring.

The terminating point of the reaction can be confirmed by various analytical means such as thin-layer chromatography, gas chromatography or high-speed liquid chromatography.

After the reaction has been finished, after-treatments are conducted, such as extracting the solvent, filtration and washing, followed by refining to obtain a desired aromatic amino compound, i.e., an aromatic amino compound of a structure in which an aromatic ring group derived from the halogenated aromatic compound is coupled to the part of the amino group (NH group) of the starting amine compound.

The refining can be conducted by a column chromatography method, an adsorptive isolation method by using silica gel, activated carbon or activated clay, or a recrystallization or crystallization method.

According to the above-mentioned method of the invention, the desired aromatic amino compound is obtained in high yields by reacting the starting amine compound with the halogenated aromatic compound under the condition where the aromatic oxycarboxylic acid having a hydroxyl group and a hydroxycarbonyl group that are bonded to the neighboring carbon atoms thereof, is made present together with the copper catalyst and the base.

The aromatic oxycarboxylic acid such as 2-hydroxybenzenecarboxylic acid used in the method is available at a low cost and, besides, the reaction can be carried out without using any special operation or apparatus, offering great advantage from the standpoint of production cost and putting the method into practice on an industrial scale.

EXAMPLES

The present invention will now be described by way of Examples to which only, however, the invention is in no way limited.

Example 1

Synthesis of a 4,4'-bis{(biphenyl-4-il)-phenylamino}biphenyl

The following compounds were put into a reaction vessel purged with nitrogen and were mixed together.

| | |
|---|---|
| (Biphenyl-4-il)-phenylamine | 8.50 g (34.6 millimols) |
| 4,4'-Diiodobiphenyl | 5.85 g (14.4 millimols) |
| Copper powder | 0.09 g (1.44 millimols) |
| 3,5-Di(tert-butyl)-2-hydroxybenzenecarboxylic acid | 0.36 g (1.44 millimols) |
| Potassium carbonate | 5.97 g (43.2 millimols) |
| Sodium hydrogensulfite | 0.45 g (4.32 millimols) |
| Dodecylbenzene | 10 ml |
| Xylene | 20 ml |

The above mixture put into the reaction vessel was heated at 210° C. for 11 hours with stirring while distilling off xylene.

After the reaction has been finished, the obtained reaction solution was analyzed by the HPLC to confirm the terminating point of the reaction. The HPLC analyzer possessed the following specifications.

HPLC analyzer: Model L-7100 manufactured by Hitachi, Ltd.

Column: Inertsil ODS-3 manufactured by GL Science Co., 4.6 mm in inner diameter, 250 mm in length, Flow rate: 1.0 ml/min, Column temperature: 40° C., Detection wavelength: 254 nm Eluent: acetonitrile/THF=9/1 (v/v)

The results of HPLC analysis at the terminating point of the reaction were as described below in terms of the peak area ratios of the HPLC.

4,4'-Bis{(biphenyl-4-il)-phenylamino}biphenyl (object product): 90.6%

4,4'-Diiodobiphenyl (starting material): 0.64%

Monoiodide (intermediate product): 0.75%

The above reaction solution was cooled, toluene was added thereto to remove undissolved matters by filtration, and the filtrate was concentrated to obtain a concentrated product thereof.

Hexane was added to the concentrated product, precipitated crystals were picked up by filtration, the obtained coarse crystals were refined by crystallization by using a mixed solvent of toluene/hexane to obtain an object 4,4'-bis{(biphenyl-4-il)-phenylamino}biphenyl in powdery form in an amount of 8.46 g (yield, 91.7%).

The obtained powder was put to the NMR analysis (1H-NMR) to confirm the structure. A chart of analysis thereof is shown in FIG. 1.

Example 2

Synthesis of an N,N'-bis(4-diphenylamino-biphenyl-4'-il)-N,N'-diphenyl-9,9-bis(4-aminophenyl)fluorene The following compounds were put into the reaction vessel purged with nitrogen and were mixed together.

| | |
|---|---|
| 9,9-Bis(4-iodophenyl)fluorene | 30.0 g (52.6 millimols) |
| 4-(Diphenylamino-biphenyl-4'-il)phenylamine | 52.09 g (126.3 millimols) |
| Copper powder | 0.34 g (5.35 millimols) |
| 3,5-Di(tert-butyl)-2-hydroxybenzenecarboxylic acid | 1.34 g (5.35 millimols) |
| Potassium carbonate | 21.81 g (157.8 millimols) |
| Sodium hydrogensulfite | 1.65 g (15.8 millimols) |
| Dodecylbenzene | 50 ml |

The above mixture put into the reaction vessel was heated with stirring. After stirred at 200° C. for 9 hours, there were, further, added:

| | |
|---|---|
| Copper powder | 0.34 g (5.35 millimols), |
| Potassium carbonate | 7.26 g (52.5 millimols), | and the mixture was, further, stirred at 200° C. for 6 hours.

After the reaction has been finished, the obtained reaction solution was analyzed by the HPLC to confirm the terminating point of the reaction. The HPLC analyzer possessed the following specifications.

HPLC analyzer: Model LC-2010 manufactured by Shimazu Co.

Column: Inertsil ODS-3 manufactured by GL Science Co., 4.6 mm in inner diameter, 250 mm in length, Flow rate: 1.0 ml/min, Column temperature: 40° C., Detection wavelength: 254 nm Eluent: methanol/THF=8/2 (v/v)

The results of HPLC analysis at the terminating point of the reaction were as described below in terms of the peak area ratios of the HPLC.

N,N'-Bis(4-diphenylamino-biphenyl-4'-il)-N,N'-diphenyl-9,9-bis(4-aminophenyl)fluorene (object product): 75.9%

9,9-Bis(4-iodophenyl)fluorene (starting material); 0%

Monoiodide (intermediate product): 0.3%

Example 3

Synthesis of a 9,9-bis(4-diphenylaminophenyl)fluorene

The following compounds were put into the reaction vessel purged with nitrogen and were mixed together.

| | |
|---|---|
| Diphenylamine | 17.8 g (105 millimols) |
| 9,9-Bis(4-iodophenyl)fluorene | 25.0 g (43.8 millimols) |
| Copper powder | 0.28 g (4.4 millimols) |
| 3,5-Di(tert-butyl)-2-hydroxybenzenecarboxylic acid | 1.10 g (4.4 millimols) |
| Potassium carbonate | 18.1 g (131 millimols) |
| Sodium hydrogensulfite | 1.37 g (13.1 millimols) |
| Dodecylbenzene | 20 ml |

The above mixture put into the reaction vessel was heated at 200° C. for 12 hours with stirring.

After the reaction has been finished, the obtained reaction solution was analyzed by the HPLC to confirm the terminating point of the reaction. The HPLC analyzer possessed the following specifications.

HPLC analyzer: Model LC-10A manufactured by Shimazu Co.

Column: Inertsil ODS-3 manufactured by GL Science Co., 4.6 mm in inner diameter, 250 mm in length, Flow rate: 1.0 ml/min, Column temperature: 40° C., Detection wavelength: 254 nm Eluent: methanol/THF=9/1 (v/v)

The results of HPLC analysis at the terminating point of the reaction were as described below in terms of the peak area ratios of the HPLC.

9,9-Bis(4-diphenylaminophenyl)fluorene (object product): 81.8%

9,9-Bis(4-iodophenyl)fluorene (starting material): 0%

Monoiodide (intermediate product): 0%

Example 4

Synthesis of a 9,9-bis{4-bis(biphenyl-4-il)aminophenyl}fluorene

The following compounds were put into the reaction vessel purged with nitrogen and were mixed together.

| | |
|---|---|
| Bis(biphenyl-4-il)amine | 20.30 g (63.16 millimols) |
| 9,9-Bis(4-iodophenyl)fluorene | 15.00 g (26.31 millimols) |
| Copper powder | 0.17 g (2.63 millimols) |
| 3,5-Di(tert-butyl)-2-hydroxybenzenecarboxylic acid | 0.66 g (2.63 millimols) |
| Potassium carbonate | 10.91 g (78.92 millimols) |
| Sodium hydrogensulfite | 0.83 g (7.89 millimols) |
| Dodecylbenzene | 30 ml |

The above mixture put into the reaction vessel was heated at 200° C. for 13 hours with stirring.

After the reaction has been finished, the obtained reaction solution was analyzed by the HPLC to confirm the terminating point of the reaction. The HPLC analyzer possessed the following specifications.

HPLC analyzer: Model LC-6A manufactured by Shimazu Co.

Column: Inertsil ODS-3 manufactured by GL Science Co., 4.6 mm in inner diameter, 250 mm in length, Flow rate: 1.0 ml/min, Column temperature: 40° C., Detection wavelength: 254 nm Eluent: methanol/THF=85/15 (v/v)

The results of HPLC analysis at the terminating point of the reaction were as described below in terms of the peak area ratios of the HPLC.

9,9-Bis{4-bis(biphenyl-4-il)aminophenyl}fluorene (object product): 49.8%

9,9-Bis(4-iodophenyl)fluorene (starting material): 2.8%

Monoiodide (intermediate product): 0.9%

Example 5

Synthesis of an N,N,N',N'-tetrakis(biphenyl-4-il)-3,3'-dimethyl-4,4'-diaminobiphenyl The following compounds were put into the reaction vessel purged with nitrogen and were mixed together.

| | |
|---|---|
| Bis(biphenyl-4-il)amine | 20.0 g (62.2 millimols) |
| 3,3'-Dimethyl-4,4'-diiodobiphenyl | 11.24 g (25.9 millimols) |
| Copper powder | 0.16 g (2.59 millimols) |
| 3,5-Di(tert-butyl)-2-hydroxybenzenecarboxylic acid: | 0.65 g (2.59 millimols) |
| Potassium carbonate | 10.74 g (77.7 millimols) |
| Sodium hydrogensulfite | 0.81 g (7.77 millimols) |
| Dodecylbenzene | 24 ml |
| Xylene: | 48 ml |

The above mixture put into the reaction vessel was heated at 210° C. for 7.5 hours with stirring while distilling off xylene. Thereafter, there were, further, added:

| | |
|---|---|
| Copper powder | 0.16 g (2.59 millimols), |
| Potassium carbonate | 3.58 g (25.9 millimols), | and the mixture was, further, stirred at 210° C. for 6 hours.

After the reaction has been finished, the obtained reaction solution was analyzed by the HPLC to confirm the terminating point of the reaction. The HPLC analyzer possessed the following specifications.

HPLC analyzer: Model L-7100 manufactured by Hitachi, Ltd.
  Column: Inertsil ODS-3 manufactured by GL Science Co., 4.6 mm in inner diameter, 250 mm in length,
  Flow rate: 1.0 ml/min,
  Column temperature: 40° C.,
  Detection wavelength: 254 nm
  Eluent: acetonitrile/THF=85/15 (v/v)

The results of HPLC analysis at the terminating point of the reaction were as described below in terms of the peak area ratios of the HPLC.

N,N,N',N'-tetrakis(biphenyl-4-il)-3,3'-dimethyl-4,4'-diaminobiphenyl (object product): 78.8%

3,3'-Dimethyl-4,4'-diiodobiphenyl (starting material): 2.1%

Monoiodide (intermediate product): 0.52%

Example 6

Synthesis of a 4,4'-bis{(biphenyl-4-il)-phenylamino}-3,3'-dimethylbiphenyl

The following compounds were put into the reaction vessel purged with nitrogen and were mixed together.

| | |
|---|---|
| (Biphenyl-4-il)-phenylamine | 26.41 g (107.6 millimols) |
| 3,3'-Dimethyl-4,4'-diiodobiphenyl | 19.47 g (44.85 millimols) |
| Copper powder | 0.29 g (4.49 millimols) |
| 4-Methyl-2-hydroxybenzenecarboxylic acid: | 0.68 g (4.49 millimols) |
| Potassium carbonate | 18.60 g (134.6 millimols) |
| Sodium hydrogensulfite | 1.41 g (13.46 millimols) |
| Dodecylbenzene | 39 ml |

The above mixture put into the reaction vessel was heated at 200: for 18 hours with stirring.

After the reaction has been finished, the obtained reaction solution was analyzed by the HPLC to confirm the terminating point of the reaction. The HPLC analyzer possessed the following specifications.

HPLC analyzer: Model L-7100 manufactured by Hitachi, Ltd.
  Column: Inertsil ODS-3 manufactured by GL Science Co., 4.6 mm in inner diameter, 250 mm in length,
  Flow rate: 1.0 ml/min,
  Column temperature: 40° C.,
  Detection wavelength: 254 nm
  Eluent: methanol/THF=9/1 (v/v)

The results of HPLC analysis at the terminating point of the reaction were as described below in terms of the peak area ratios of the HPLC.

4,4'-Bis{(biphenyl-4-il)-phenylamino}-3,3'-dimethylbiphenyl (object product): 85.6%

3,3'-Dimethyl-4,4'-diiodobiphenyl (starting material): 4.5%

Monoiodide (intermediate product): 1.6%

Example 7

Synthesis of the 9,9-bis(4-diphenylaminophenyl)fluorene

The reaction was carried out under the same conditions as those of Example 3 but using a 2-hydroxybenzenecarboxylic acid instead of the 3,5-di(tert-butyl)-2-hydroxybenzenecarboxylic acid.

After the reaction has been finished, the obtained reaction solution was analyzed to confirm the terminating point of the reaction by using the HPLC analyzer of the same specifications as those of Example 3. The results of HPLC analysis were as described below in terms of the peak area ratios of the HPLC.

9,9-Bis(4-diphenylaminophenyl)fluorene (object product): 81.2%

9,9-Bis(4-iodophenyl)fluorene (starting material): 0%

Monoiodide (intermediate product): 0.2%

Example 8

Synthesis of the 9,9-Bis(4-diphenylaminophenyl)fluorene

The reaction was carried out under the same conditions as those of Example 3 but using a 5-cyclohexyl-2-hydroxybenzenecarboxylic acid instead of the 3,5-di(tert-butyl)-2-hydroxybenzenecarboxylic acid.

After the reaction has been finished, the obtained reaction solution was analyzed to confirm the terminating point of the reaction by using the HPLC analyzer of the same specifications as those of Example 3. The results of HPLC analysis were as described below in terms of the peak area ratios of the HPLC.

9,9-Bis(4-diphenylaminophenyl)fluorene (object product): 81.0%

9,9-Bis(4-iodophenyl)fluorene (starting material): 0%

Monoiodide (intermediate product): 0.1%

Example 9

Synthesis of the 9,9-bis(4-diphenylaminophenyl)fluorene

The reaction was carried out under the same conditions as those of Example 3 but using a 5-methoxy-2-hydroxybenzenecarboxylic acid instead of the 3,5-di(tert-butyl)-2-hydroxybenzenecarboxylic acid.

After the reaction has been finished, the obtained reaction solution was analyzed to confirm the terminating point of the reaction by using the HPLC analyzer of the same specifications as those of Example 3. The results of HPLC analysis were as described below in terms of the peak area ratios of the HPLC.

9,9-Bis(4-diphenylaminophenyl)fluorene (object product): 81.3%
9,9-Bis(4-iodophenyl)fluorene (starting material): 0%
Monoiodide (intermediate product): 0.1%

Example 10

Synthesis of the 9,9-bis(4-diphenylaminophenyl)fluorene

The reaction was carried out under the same conditions as those of Example 3 but using a 4-fluoro-2-hydroxybenzenecarboxylic acid instead of the 3,5-di(tert-butyl)-2-hydroxybenzenecarboxylic acid.

After the reaction has been finished, the obtained reaction solution was analyzed to confirm the terminating point of the reaction by using the HPLC analyzer of the same specifications as those of Example 3. The results of HPLC analysis were as described below in terms of the peak area ratios of the HPLC.

9,9-Bis(4-diphenylaminophenyl)fluorene (object product): 81.5%
9,9-Bis(4-iodophenyl)fluorene (starting material): 0%
Monoiodide (intermediate product): 0%

Example 11

Synthesis of the 9,9-bis(4-diphenylaminophenyl)fluorene

The reaction was carried out under the same conditions as those of Example 3 but using a 4-phenyl-2-hydroxybenzenecarboxylic acid instead of the 3,5-di(tert-butyl)-2-hydroxybenzenecarboxylic acid.

After the reaction has been finished, the obtained reaction solution was analyzed to confirm the terminating point of the reaction by using the HPLC analyzer of the same specifications as those of Example 3. The results of HPLC analysis were as described below in terms of the peak area ratios of the HPLC.

9,9-Bis(4-diphenylaminophenyl)fluorene (object product): 80.9%
9,9-Bis(4-iodophenyl)fluorene (starting material): 0%
Monoiodide (intermediate product): 0.1%

Example 12

Synthesis of the 9,9-bis(4-diphenylaminophenyl)fluorene

The reaction was carried out under the same conditions as those of Example 3 but using a 5-(pyridine-2-il)-2-hydroxybenzenecarboxylic acid instead of the 3,5-di(tert-butyl)-2-hydroxybenzenecarboxylic acid.

After the reaction has been finished, the obtained reaction solution was analyzed to confirm the terminating point of the reaction by using the HPLC analyzer of the same specifications as those of Example 3. The results of HPLC analysis were as described below in terms of the peak area ratios of the HPLC.

9,9-Bis(4-diphenylaminophenyl)fluorene (object product): 80.4%
9,9-Bis(4-iodophenyl)fluorene (starting material): 0%
Monoiodide (intermediate product): 0.3%

Example 13

Synthesis of the 9,9-bis(4-diphenylaminophenyl)fluorene

The reaction was carried out under the same conditions as those of Example 3 but using a 1-hydroxynaphthalene-2-carboxylic acid instead of the 3,5-di(tert-butyl)-2-hydroxybenzenecarboxylic acid.

After the reaction has been finished, the obtained reaction solution was analyzed to confirm the terminating point of the reaction by using the HPLC analyzer of the same specifications as those of Example 3. The results of HPLC analysis were as described below in terms of the peak area ratios of the HPLC.

9,9-Bis(4-diphenylaminophenyl)fluorene (object product): 81.0%
9,9-Bis(4-iodophenyl)fluorene (starting material): 0%
Monoiodide (intermediate product): 0.1%

Example 14

Synthesis of a 9,9-bis{4-(carbazolyl-9-il)-phenyl}fluorene

The following compounds were put into the reaction vessel purged with nitrogen and were mixed together.

| | |
|---|---|
| Carbazole | 19.3 g (115 millimols) |
| 9,9-Bis(4-iodophenyl)fluorene | 29.9 g (52.4 millimols) |
| Copper powder | 0.33 g (5.2 millimols) |
| 3,5-Di(tert-butyl)-2-hydroxybenzenecarboxylic acid | 1.31 g (5.2 millimols) |
| Potassium carbonate | 21.7 g (157 millimols) |
| Sodium hydrogensulfite | 1.64 g (15.7 millimols) |
| Dodecylbenzene | 33 ml |
| Xylene | 66 ml |

The above mixture put into the reaction vessel was heated at 195° C. for 4 hours with stirring while distilling off xylene. Thereafter, there were, further, added:

| | |
|---|---|
| Copper powder | 0.33 g (5.2 millimols) |
| Potassium carbonate | 0.72 g (5.2 millimols) | and the mixture was, further, stirred at 195° C. for 6 hours.

After the reaction has been finished, the obtained reaction solution was analyzed by the HPLC to confirm the terminating point of the reaction. The HPLC analyzer possessed the following specifications.

HPLC analyzer: Model CCPD manufactured by Toso Co.
Column: Inertsil ODS-3 manufactured by GL Science Co., 4.6 mm in inner diameter, 250 mm in length,
Flow rate: 1.0 ml/min,
Column temperature: 40° C.,
Detection wavelength: 254 nm
Eluent: methanol/THF=9/1 (v/v)

The results of HPLC analysis at the terminating point of the reaction were as described below in terms of the peak area ratios of the HPLC.

9,9-Bis{4-(carbazolyl-9-il)-phenyl}fluorene (object product): 72.4%
9,9-Bis(4-iodophenyl)fluorene (starting material): 1.0%
Monoiodide (intermediate product): 1.9%

Example 15

Synthesis of a 3,5-bis[6-(carbazolyl-9-il)-pyridine-2-il]-4-phenyl-4H-[1,2,4]triazole The following compounds were put into the reaction vessel purged with nitrogen and were mixed together.

| | |
|---|---|
| Carbazole | 16.9 g (101 millimols) |
| 3,5-Bis(6-chloropyridine-2-il)-4-phenyl-4H-[1,2,4]triazole | 14.3 g (38.8 millimols) |
| Copper powder | 0.25 g (3.9 millimols) |
| 3,5-Di(tert-butyl)-2-hydroxybenzenecarboxylic acid | 0.97 g (3.9 millimols) |
| Potassium carbonate | 16.1 g (117 millimols) |
| Dodecylbenzene | 40 ml |

The above mixture put into the reaction vessel was heated with stirring. After stirred at 205 to 215° C. for 4.5 hours, there were, further, added:

| | |
|---|---|
| Copper powder | 0.25 g (3.9 millimols), |
| Potassium carbonate | 5.4 g (39 millimols), |
| Xylene | 20 ml | and the mixture was, further, stirred at 210° C. for 10 hours while distilling off xylene.

After the reaction has been finished, the obtained reaction solution was analyzed by the HPLC to confirm the terminating point of the reaction. The HPLC analyzer possessed the following specifications.

HPLC analyzer: Model LC-10A manufactured by Shimazu Co.
Column: Inertsil ODS-SP manufactured by GL Science Co., 4.6 mm in inner diameter, 250 mm in length,
Flow rate: 1.0 ml/min,
Column temperature: 40° C.,
Detection wavelength: 254 nm
Eluent: methanol/0.05% TFA aqueous solution=9/1 (v/v)

The results of HPLC analysis at the terminating point of the reaction were as described below in terms of the peak area ratios of the HPLC.

3,5-Bis[6-(carbazolyl-9-il)-pyridine-2-il]-4-phenyl-4H-[1,2,4]triazole (object product): 50.0%
3,5-Bis(6-chloropyridine-2-11)-4-phenyl-4H-[1,2,4]triazole (starting material): 0%
Monochloro isomer (intermediate product): 0.1%
Carbazole: 34.2%

COMPARATIVE EXAMPLES

Comparative Example 1

The reaction was carried out in the same manner and under the same conditions as those of Example 1 but feeding the starting materials in amounts twice as much and without adding the 3,5-di(tert-butyl)-2-hydroxybenzenecarboxylic acid.

The terminating point of the reaction was confirmed by the HPLC to learn that a time of 20.5 hours was needed until the terminating point of the reaction was reached.

The reaction solution at the terminating point of the reaction was analyzed by the HPLC under the same measuring conditions as those of Example 1.

The peak area ratios of the HPLC at the terminating point of the reaction were as follows:

4,4'-Bis{(biphenyl-4-il)-phenylamino}biphenyl (object product): 87.9%
4,4'-Diiodobiphenyl (starting material): 0.55%
Monoiodide (intermediate product): 0.32%

Upon conducting the after-treatment and the refining operation under the same conditions as those of Example 1, there was obtained the object 4,4'-bis{(biphenyl-4-il)-phenylamino}biphenyl in powdery form in an amount of 16.84 g (yield, 91.0%).

Comparative Example 2

The reaction was carried out in the same manner and under the same conditions as those of Example 2 but without adding the 3,5-di(tert-butyl)-2-hydroxybenzenecarboxylic acid.

That is, the following compounds were put into the reaction vessel purged with nitrogen and were mixed together.

| | |
|---|---|
| 9,9-Bis(4-iodophenyl)fluorene | 30.0 g (52.6 millimols) |
| 4-(Diphenylamino-biphenyl-4'-il)-phenylamine | 52.09 g (126.3 millimols) |
| Copper powder | 0.34 g (5.35 millimols) |
| Potassium carbonate | 21.81 g (157.8 millimols) |
| Sodium hydrogensulfite | 1.65 g (15.8 millimols) |
| Dodecylbenzene | 50 ml |

The above mixture put into the reaction vessel was heated at 210° C. for 16 hours with stirring. Thereafter, there were, further, added:

| | |
|---|---|
| Copper powder | 0.34 g (5.35 millimols) |
| Potassium carbonate | 7.26 g (52.5 millimols) | and the mixture was, further, stirred at 210° C. for 9 hours. Since the reaction was sluggish, there were, further, added:

| | |
|---|---|
| Copper powder | 0.34 g (5.35 millimols) |
| Potassium carbonate | 7.26 g (52.5 millimols) | and the temperature was elevated to 225° C. and the reaction was carried out for another 8 hours with stirring. Since the reaction was still sluggish, there were, further, added:

| | |
|---|---|
| Copper powder | 0.34 g (5.35 millimols) |
| Potassium carbonate | 7.26 g (52.5 millimols) | and the mixture was stirred at 225° C. for 3.5 hours.

The reaction solution was analyzed by the HPLC under the same measuring conditions as those of Example 2.

The peak area ratios of the HPLC at the terminating point of the reaction were as follows:
 N,N'-Bis(4-diphenylamino-biphenyl-4'-il)-N,N'-diphenyl-9,9-bis(4-aminophenyl)fluorene (object product): 72.0%
 9,9-Bis(4-iodophenyl)fluorene (starting material): 0%
 Monoiodide (intermediate product): 0%

The results of the above Examples and Comparative Examples tell that upon making the aromatic oxycarboxylic acid (of which a hydroxyl group and a hydroxycarbonyl group are bonded to the neighboring carbon atoms thereof) present together with a copper catalyst and a base, activity of the copper catalyst can be improved, the reaction time can be shortened to less than one-half and, besides, the Ullmann reaction can be conducted even at relatively low temperatures.

INDUSTRIAL APPLICABILITY

According to the present invention, the Ullmann reaction is carried out by using an amine compound and a halogenated aromatic compound as starting materials in the presence of a copper catalyst, a base and a solvent, the Ullmann reaction being carried out in the presence of an aromatic oxycarboxylic acid having a hydroxyl group and a hydroxycarbonyl group bonded to the neighboring carton atoms thereof, making it possible to shorten the reaction time and to lower the reaction temperature. Therefore, aromatic amino compounds useful as various organic materials or as intermediate products therefor can be produced in high yields, in high purities and at low costs.

The invention claimed is:

1. A method of producing an aromatic amino compound by using, as starting materials,
 an amine compound selected from a compound represented by the following general formula (1):

R—NH—Ar  (1)

wherein
  R is a hydrogen atom or an aromatic ring group, and
  Ar is an aromatic ring group, and
 a halogenated aromatic compound; and reacting said amine compound with said halogenated aromatic compound in the presence of a copper catalyst and a base so as to produce the aromatic amino compound having a structure in which an aromatic ring group derived from said halogenated aromatic compound is coupled to the amino group of said amine compound;
 wherein said amine compound and said halogenated aromatic compound are reacted together under a condition where an aromatic oxycarboxylic acid having a hydroxyl group and a hydroxycarbonyl group that are bonded to the neighboring carbon atoms thereof, is made present together with said copper catalyst and said base, and
 wherein
  (a) the aromatic oxycarboxylic acid is represented by the following general formula (2),

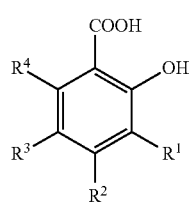

(2)

and wherein
  (b) in general formula (2), at least any one of the groups $R^1$ to $R^4$ is an alkyl group having 2 to 6 carbon atoms, an alkyloxy group having 1 to 6 carbon atoms, a cycloalkyl group having 5 to 8 carbon atoms, an aromatic hydrocarbon group, an aromatic heterocyclic group or a fluorine atom;
 and
  (c) the aromatic oxycarboxylic acid is used in an amount of 0.8 to 3 moles per mol of the copper catalyst.

2. The method of producing an aromatic amino compound according to claim 1, wherein the halogen atom of said halogenated aromatic compound is iodine, bromine or chlorine.

3. The method of producing an aromatic amino compound according to claim 2, wherein said halogenated aromatic compound is an aryl iodide, an aryl bromide or an aryl chloride.

4. The method of producing an aromatic amino compound according to claim 1, wherein said starting amine compound is monoarylamine or diarylamine.

5. The method of producing an aromatic amino compound according to claim 1, wherein in said general formula (2), at least one of the groups $R^1$ to $R^4$ is a straight-chain or branched-chain alkyl group having 2 to 6 carbon atoms, a cycloalkyl group having 5 to 8 carbon atoms, an aromatic hydrocarbon group or an aromatic heterocyclic ring group.

6. The method of producing an aromatic amino compound according to claim 5, wherein said aromatic oxycarboxylic acid is a 3,5-di-tert-butyl-2-hydroxybenzenecarboxylic acid.

7. The method of producing an aromatic compound according to claim 1, wherein the alkloxy group is a methoxy group.

* * * * *